United States Patent
Chen et al.

(10) Patent No.: US 9,611,276 B2
(45) Date of Patent: Apr. 4, 2017

(54) IMIDAZO BICYCLIC IMINIUM COMPOUNDS AS ANTITUMOR AGENTS

(71) Applicant: THE BOARD OF TRUSTEES OF THE LELAND STANFORD JUNIOR UNIVERSITY, Stanford, CA (US)

(72) Inventors: James Chen, Mountain View, CA (US); Tomoyo Sakata Kato, Sunnyvale, CA (US); Alison Evelynn Ondrus, San Francisco, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 3 days.

(21) Appl. No.: 14/409,683

(22) PCT Filed: Jun. 19, 2013

(86) PCT No.: PCT/US2013/046560
§ 371 (c)(1),
(2) Date: Dec. 19, 2014

(87) PCT Pub. No.: WO2013/192301
PCT Pub. Date: Dec. 27, 2013

(65) Prior Publication Data
US 2015/0191489 A1    Jul. 9, 2015

Related U.S. Application Data

(60) Provisional application No. 61/662,977, filed on Jun. 22, 2012.

(51) Int. Cl.
| C07D 515/04 | (2006.01) |
| C07D 513/04 | (2006.01) |
| A61K 31/437 | (2006.01) |
| C07D 471/04 | (2006.01) |
| C07D 487/04 | (2006.01) |
| A61K 31/4188 | (2006.01) |
| A61K 31/429 | (2006.01) |
| A61K 31/5383 | (2006.01) |
| A61K 31/55 | (2006.01) |
| C07D 498/04 | (2006.01) |

(52) U.S. Cl.
CPC ........ C07D 513/04 (2013.01); A61K 31/4188 (2013.01); A61K 31/429 (2013.01); A61K 31/437 (2013.01); A61K 31/5383 (2013.01); A61K 31/55 (2013.01); C07D 471/04 (2013.01); C07D 487/04 (2013.01); C07D 498/04 (2013.01)

(58) Field of Classification Search
CPC .................................................. C07D 515/04
See application file for complete search history.

(56) References Cited

FOREIGN PATENT DOCUMENTS

| WO | 00/53600 | 9/2000 |
| WO | 2007025751 A1 | 3/2007 |
| WO | 2008064136 A2 | 5/2008 |
| WO | 2010/129620 | 11/2010 |

OTHER PUBLICATIONS

American Chemical Society. © Nov. 27, 2002. STN Database. RN 474647-84-2.*
V.A. Chumakov et al; "Synthesis and study of the analgesic and antiinflammatory activity of imidazo[2,1-b] thiazolium bromides," Pharmaceutical Chemistry Journal, 1999, vol. 33, No. 8, pp. 421-423.
A.M. Demchenko et al; "On the reaction of 2-phenylaminothiazoline with a-halogenoketones," Chemistry of Heterocyclic Compounds, 1997, vol. 33, No. 6, pp. 724-727.
A.M. Demchenko et al; "Synthesis and Structure of Quarternary Salts Derived from 2-Anilino- and 2-Benzylamino-5, 6-dihydro-4H-1, 3-thiazine," Russian Journal of General Chemistry, 2001, vol. 71, No. 11, pp. 1759-1763.

(Continued)

Primary Examiner — Noble Jarrell
Assistant Examiner — John S Kenyon
(74) Attorney, Agent, or Firm — Heslin Rothenberg Farley & Mesiti, P.C.; Philip Hansen

(57) ABSTRACT

Compounds of formula I:

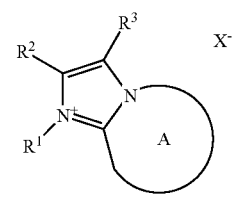

are disclosed. The compounds are inhibitors of Hedgehog pathway activation and are useful in treating solid tumors. An example of such a compound is:

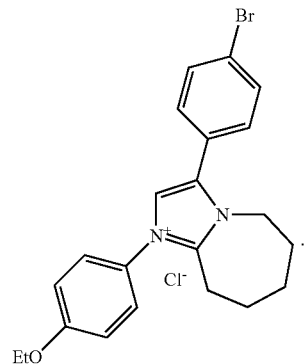

8 Claims, No Drawings

(56) References Cited

OTHER PUBLICATIONS

International Search Report for PCT/US2013/046560 dated Nov. 1, 2013.
Stanley, et al., Identification of Novel Inhibitors of M. tuberculosis Growth Using Whole Cell Based High-, Throughout Screening, American Chemical Society, May 11, 2012.
Demchenko, et al., Synthesis and Properties of 1,3-Diaryl-5,6-Dihydro-8H-Imidazo[2,1-C]-1,4-Oxazinium Bromides, Chemistry Compounds, vol. 39, No. 8, 2003.
Sizaya, et al., Inhibiting Action of 1,2-Diaryl-5,6-Dihydroimyidazo[2,1-*b*]-Thiazolium Bromides on Acid Corrosion of Steel, Russian Journal of Applied Chemistry, vol. 69, No. 9, 1996, pp. 1342-1345, Translated from Zhurnal Prikiadnoi Khimii, vol. 69, No. 9, 1996, pp. 1501-1504
Shtil, et al, Reactions of 3-Amino-Substituted 5,6-Dihydro-2H-1,4-Oxazines With *a*-Halo Ketones, Chemistry of Heterocyclic Compounds, vol. 37, No. 8, 2001.
Peters, et al., An Isogenic Cell Panel Identifies Compounds That Inhibit Proliferation of mTOR-Pathway Addicted Cells by Different Mechanisms, Journal of Biomolecular Screening, 2014, col. 19(1) 131-144.
Supplemental European Search Report from EP 13 80 7852 (Feb. 4, 2015).

\* cited by examiner

IMIDAZO BICYCLIC IMINIUM COMPOUNDS AS ANTITUMOR AGENTS

CROSS-REFERENCE TO RELATED APPLICATIONS

This application is a national phase filing under 35 U.S.C. §371 of PCT International Application PCT/US2013/046560, filed Jun. 19, 2013, and published under PCT Article 21(2) as WO 2013/192301 on Dec. 27, 2013. PCT/US2013/046560 claims priority from U.S. provisional application 61/662,977, filed Jun. 22, 2012. The contents of each of the prior applications are incorporated herein by reference in their entirety.

FEDERALLY SPONSORED RESEARCH

This invention was made with Government support under contract CA136574 awarded by the National Institutes of Health. The Government has certain rights in this invention.

FIELD OF THE INVENTION

The invention relates to imidazobicycles having a quaternary nitrogen that are inhibitors of the Hedgehog pathway and therefore useful as antitumor agents and as probes of the function of Hedgehog-dependent systems.

BACKGROUND OF THE INVENTION

The Hedgehog (Hh) pathway plays a critical role in the patterning, homeostasis, and oncogenic transformation of multiple tissues. For example, Hh signaling regulates cerebellar patterning and growth, and Hh pathway activation is a leading cause of medulloblastoma, the most common pediatric brain cancer. Genetic screens have revealed a number of Hh pathway regulators, including canonical signaling proteins that are conserved across metazoans and vertebrate-specific modulators. These studies have provided a general framework for vertebrate Hh signal transduction, which in mammals is initiated by the binding of secreted polypeptides (Sonic, Shh; Indian, Ihh; or Desert, Dhh) to the 12-transmembrane receptor Patched1 (Ptch1) and the subsequent activation of Smoothened (Smo), a G protein-coupled receptor-like protein. Smo then acts through unknown mechanisms to control the functions of Gli2 and Gli3, zinc finger transcription factors that exist as a balance between N-terminal repressors (Gli2/3R), full-length proteins (Gli2/3FL), or phosphorylated forms of Gli2/3FL that are transcriptionally active (Gli2/3A). This process is mediated at least in part by Suppressor of Fused (Sufu), a direct negative regulator of Gli function. The primary cilium serves as a Hh pathway nexus; Ptch1, Smo, Sufu, Gli2, and Gli3 traffic through the cilium in a pathway activity-dependent manner, and many of their interactions appear to occur within or depend upon this microtubule-scaffolded structure. Upon Hh pathway activation, Gli2A and to a lesser extent Gli3A then drive the transcription of Hh target genes, including Ptch1 and the constitutively active factor Gli1.

The therapeutic utility of Hh pathway inhibitors has been confirmed by the recent approval of vismodegib (ERIVEDGE™) by the U.S. Food and Drug Administration. It is currently indicated for patients with basal cell carcinoma. Vismodegib is also undergoing clinical trials for metastatic colorectal cancer, small-cell lung cancer, advanced stomach cancer, pancreatic cancer, chondrosarcoma and medulloblastoma. Vismodegib acts as an antagonist of the Smoothened receptor (SMO). SMO inhibition causes the transcription factors GLI1 and GLI2 to remain inactive, which prevents the expression of tumor-mediating genes within the Hedgehog pathway. This pathway is pathogenetically relevant in more than 90% of basal cell carcinomas.

Current SMO-targeting therapies, despite their promise, have some potential drawbacks. Hh signaling is an important regulator of bone growth in juvenile mice, and Smo inhibitors cause permanent dwarfism in animal models. While such pharmacological side effects may be outweighed by the pernicious nature of certain Hh pathway-induced cancers, the side effects may warrant contraindication in other cases. New Hh pathway inhibitors, including those that act through different mechanisms, are needed to address these challenges.

In addition to their potential utility in treating tumors, small-molecule inhibitors of the Hh pathway can be valuable tools for studying Hh signaling mechanisms.

SUMMARY OF THE INVENTION

In one aspect, the invention relates to a method of inhibiting Hedgehog pathway activation comprising bringing a cell that is capable of Hedgehog expression into contact with a compound of formula I:

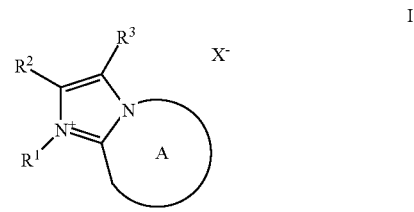

wherein:

$R^1$ is chosen from optionally substituted aryl and optionally substituted heteroaryl;

$R^2$ is chosen from H, halogen, $(C_1$-$C_4)$alkyl, halo$(C_1$-$C_4)$alkyl, optionally substituted aryl and optionally substituted heteroaryl;

$R^3$ is chosen from H, alkyl, optionally substituted aryl and optionally substituted heteroaryl;

A is (a) a fused, saturated ring of 5 to 7 members that may contain other heteroatoms in addition the nitrogen at the point of fusion, said saturated ring optionally substituted with one or two $(C_1$-$C_4)$alkyl residues or (b) a fused bicycle, at least one ring of said fused bicycle being non-aromatic and said bicycle optionally substituted with one or two $(C_1$-$C_4)$alkyl residues; and X is any counterion. In these compounds, one of $R^2$ and $R^3$ must be optionally substituted aryl or optionally substituted heteroaryl.

In another aspect, the invention relates to the use of a compound of formula I for inhibiting the growth of a solid tumor.

In another aspect, the invention relates to method of probing Hedgehog function in vitro comprising bringing a cell that is capable of Hedgehog expression into contact with a compound of formula I.

In another aspect, the invention relates to a pharmaceutical composition comprising a pharmaceutically acceptable carrier and a compound of formula II:

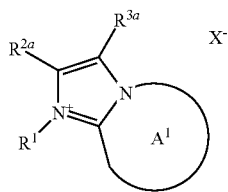

II wherein:
$R^1$ is chosen from optionally substituted aryl and optionally substituted heteroaryl;
$R^{2a}$ is chosen from H and $(C_1-C_4)$alkyl;
$R^{3a}$ is chosen from optionally substituted aryl and optionally substituted heteroaryl;
$A^1$ is (a) a fused, saturated ring of 5 to 7 members that may contain other heteroatoms in addition the nitrogen at the point of fusion, said saturated ring optionally substituted with one or two $(C_1-C_4)$alkyl residues or
(b) a fused bicycle, at least one ring of said fused bicycle being non-aromatic and said bicycle optionally substituted with one or two $(C_1-C_4)$alkyl residues; and
X is any counterion.

In another aspect, the invention relates to compounds of formula III:

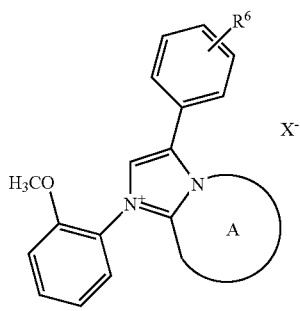

III wherein
A is (a) a fused, saturated ring of 5 to 7 members that may contain other heteroatoms in addition the nitrogen at the point of fusion, said saturated ring optionally substituted with one or two $(C_1-C_4)$alkyl residues or
(b) a fused bicycle, at least one ring of said fused bicycle being non-aromatic and said bicycle optionally substituted with one or two $(C_1-C_4)$alkyl residues;
$R^6$ is one or two substituents chosen independently from the group consisting of halogen, halo$(C_1-C_6)$alkyl, $(C_1-C_6)$alkyl, $(C_1-C_6)$acyl, $(C_1-C_6)$alkoxy$(C_1-C_6)$alkyl, hydroxy$(C_1-C_6)$alkyl, phenyl, benzenesulfonyl, hydroxy, $(C_1-C_6)$alkoxy, halo$(C_1-C_6)$alkoxy, oxaalkyl, carboxy, $(C_1-C_6)$alkoxycarbonyl, $(C_1-C_6)$alkoxycarbonylamino, carboxamido, cyano, acetoxy, nitro, amino, $(C_1-C_6)$alkylamino, $(C_1-C_6)$dialkylamino, mercapto, $(C_1-C_6)$alkylthio, $(C_1-C_6)$alkylsulfoxide, $(C_1-C_6)$alkylsulfonyl, benzyl, heterocyclyl, phenoxy, heteroaryloxy and benzyloxy, and
X is any counterion.

DETAILED DESCRIPTION OF THE INVENTION

The antitumor compounds described herein inhibit Hedgehog signaling and thereby inhibit tumor growth. The compounds that are useful in the methods described herein fall into a genus of formula I:

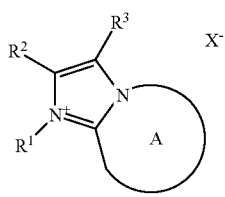

(I)

In these compounds, $R^1$ is chosen from optionally substituted aryl and optionally substituted heteroaryl. In some embodiments, $R^1$ is phenyl or optionally substituted phenyl. For example, $R^1$ may be phenyl or phenyl substituted with a substituent chosen from halogen, $(C_1-C_4)$alkyl, halo$(C_1-C_4)$alkyl, $(C_1-C_4)$alkoxy, halo$(C_1-C_4)$alkoxy, $(C_1-C_2)$alkylenedioxy and phenyl.

$R^2$ is chosen from H, halogen, $(C_1-C_4)$alkyl, halo$(C_1-C_4)$alkyl, optionally substituted aryl and optionally substituted heteroaryl. When $R^2$ is H, halogen, $(C_1-C_4)$alkyl or halo$(C_1-C_4)$alkyl, then $R^3$ must be optionally substituted aryl or optionally substituted heteroaryl.

$R^3$ may be chosen from H, alkyl, optionally substituted aryl and optionally substituted heteroaryl. In some embodiments $R^2$ is H or methyl and $R^3$ is phenyl or phenyl substituted with a substituent chosen from halogen, $(C_1-C_4)$alkyl, halo$(C_1-C_4)$alkyl, $(C_1-C_4)$alkoxy, halo$(C_1-C_4)$alkoxy, $(C_1-C_2)$alkylenedioxy, and phenyl. In some embodiments, $R^3$ is phenyl substituted with a substituent chosen from halogen, halo$(C_1-C_6)$alkyl, $(C_1-C_6)$alkyl, $(C_1-C_6)$acyl, $(C_1-C_6)$alkoxy$(C_1-C_6)$alkyl, hydroxy$(C_1-C_6)$alkyl, phenyl, benzenesulfonyl, hydroxy, $(C_1-C_6)$alkoxy, halo$(C_1-C_6)$alkoxy, oxaalkyl, carboxy, $(C_1-C_6)$alkoxycarbonyl, $(C_1-C_6)$alkoxycarbonylamino, carboxamido, cyano, acetoxy, nitro, amino, $(C_1-C_6)$alkylamino, $(C_1-C_6)$dialkylamino, mercapto, $(C_1-C_6)$alkylthio, $(C_1-C_6)$alkylsulfoxide, $(C_1-C_6)$alkylsulfonyl, benzyl, heterocyclyl, phenoxy, heteroaryloxy and benzyloxy. In other embodiments, $R^3$ is H or methyl and $R^2$ is phenyl or phenyl substituted with a substituent chosen from halogen, $(C_1-C_4)$alkyl, halo$(C_1-C_4)$alkyl, $(C_1-C_4)$alkoxy, halo$(C_1-C_4)$alkoxy, $(C_1-C_2)$alkylenedioxy, and phenyl.

Ring A may be a fused, saturated ring of 5 to 7 members. The ring may contain other heteroatoms in addition the nitrogen at the point of fusion, and it may be optionally substituted with one or two $(C_1-C_4)$alkyl residues. In addition, ring A may be a fused bicycle, at least one ring of the fused bicycle being non-aromatic. The bicycle may be optionally substituted with one or two $(C_1-C_4)$alkyl residues in either of its rings and may contain additional heteroatoms in either of its rings. In some embodiments, ring A is chosen from pyrrolidine, piperidine, azepine, thiazolidine, oxazolidine, imidazolidine, thiazine, oxazine, piperazine, oxazepine, thiazepine, diazepine and tetrahydroquinoline. In some embodiments, ring A is chosen from pyrrolidine, piperidine, azepine, thiazolidine, thiazine, morpholine and tetrahydroquinoline. For example, when ring A is azepine, the compounds of formula I are derivatives of 6,7,8,9-tetrahydro-5H-imidazo[1,2-a]azepinium:

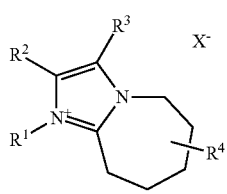

wherein $R^4$ is one or two $(C_1-C_4)$alkyl residues. Similarly, when ring A is thiazole, the compounds of formula I are derivatives of 2,3-dihydroimidazo[2,1-b]thiazolium:

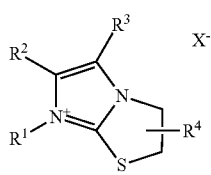

wherein $R^4$ is one or two $(C_1-C_4)$alkyl residues.

The compounds of the invention are iminium derivatives, i.e. cationic species. Therefore they will always be presented as salts, and the term "pharmaceutically acceptable salt" refers to salts whose counter ion (anion) derives from pharmaceutically acceptable non-toxic acids including inorganic acids, organic acids and water (which formally furnishes the hydroxide anion). Suitable pharmaceutically acceptable anions for the compounds of the present invention include hydroxide, acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate and the like. The desired salt may be obtained by ion exchange of whatever counter ion is obtained in the synthesis of the iminium compound. These methods are well known to persons of skill. Although pharmaceutically acceptable counter ions will be preferred for preparing pharmaceutical formulations and for use in therapeutic methods, other anions are quite acceptable as synthetic intermediates. Thus the anion may be pharmaceutically undesirable when such salts are chemical intermediates. For the purpose of therapeutic methods and pharmaceutical compositions, it is desirable that the counterion designated $X^-$ be a pharmaceutically acceptable anion.

All of the compounds falling within the foregoing parent genus and its subgenera are useful as modulators of the Hedgehog pathway and are useful for treating the cancers described below. A search of the literature indicates that certain compounds useful in the methods described herein have been disclosed for the treatment of inflammatory or obstructive airways diseases. [See US published application 2008/0207718, which discloses compounds in which ring A is pyrrolidine.] For that reason, the genus of pharmaceutical compositions is smaller than the chemical genus of compounds useful in the methods. In a composition aspect, the invention relates to a pharmaceutically acceptable carrier and a compound of formula II:

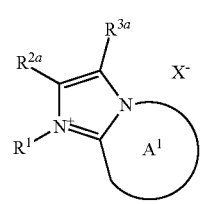

In some embodiments, $R^1$ is chosen from optionally substituted aryl and optionally substituted heteroaryl. In some embodiments, $R^1$ is phenyl or phenyl substituted with a substituent chosen from halogen, $(C_1-C_4)$alkyl, halo$(C_1-C_4)$alkyl, $(C_1-C_4)$alkoxy, halo$(C_1-C_4)$alkoxy, $(C_1-C_2)$alkylenedioxy and phenyl.

In some embodiments, $R^{2a}$ is H; in others $R^{2a}$ is $(C_1-C_4)$alkyl, such as methyl or ethyl.

In some embodiments, $R^{3a}$ is optionally substituted aryl or optionally substituted heteroaryl. In some embodiments, $R^{3a}$ is phenyl or phenyl substituted with a substituent chosen from halogen, $(C_1-C_4)$alkyl, halo$(C_1-C_4)$alkyl, $(C_1-C_4)$alkoxy, halo$(C_1-C_4)$alkoxy, $(C_1-C_2)$alkylenedioxy, and phenyl.

$A^1$ is a fused, saturated ring of 6 or 7 members that may contain other heteroatoms in addition the nitrogen at the point of fusion, and the saturated ring may be substituted with one or two $(C_1-C_4)$alkyl residues. In some embodiments, ring $A^1$ may be piperidine, azepine, thiazine, oxazine, piperazine, oxazepine, thiazepine or diazepine. In some embodiments, ring $A^1$ is azepine and a subgenus of II has the formula IIa:

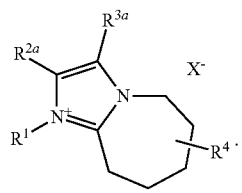

In other embodiments, ring $A^1$ is piperidine and a subgenus of II has the formula IIb:

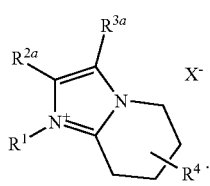

In other embodiments, ring $A^1$ is tetrahydroquinoline and a subgenus of II has the formula IIc:

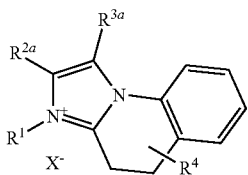

IIc

As noted above, all of the compounds falling within the parent genus I and its subgenera are useful as modulators of the Hedgehog pathway and are useful for treating the cancers described below. A search of the literature further indicates that certain compounds useful in the methods described herein have been disclosed without utility, generally from synthetic libraries, in Chemical Abstracts. Excluding such compounds, a subgenus, herein designated III, appears both novel and unexpectedly active.

Throughout this specification the terms and substituents retain their definitions.

Alkyl is intended to include linear, branched and cyclic hydrocarbon structures and combinations thereof. A combination would be, for example, cyclopropylmethyl. Any hydrocarbon in which all carbons are essentially $sp^3$ hybridized and no carbons are $sp^2$ or sp hybridized is considered alkyl. To be perfectly clear, when a substituent is ($C_1$-$C_6$) alkyl, it is meant that it can be a straight chain (for instance, methyl or ethyl), a branched chain (e.g., t-butyl), a cycloalkyl (for instance, cyclopropyl or cyclobutyl), or a combination (e.g., methylcyclopropyl). If a substituent is described more specifically, however, it takes on that definition; for instance, recitation of "cycloalkyl" refers only to a cyclic alkyl and not a linear or combination alkyl. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Cycloalkyl is a subset of alkyl and includes cyclic hydrocarbon groups of from 3 to 8 carbon atoms. Examples of cycloalkyl groups include c-propyl, c-butyl, c-pentyl, norbornyl, adamantyl and the like.

Alkoxy or alkoxyl refers to alkyl groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl means an aryl ring attached to an alkyl residue in which the point of attachment to the parent structure is through the alkyl. Examples are benzyl, phenethyl and the like. Heteroarylalkyl means an a heteroaryl ring attached through an alkyl residue to the parent structure. Examples include, e.g., pyridinylmethyl, pyrimidinylethyl and the like.

$C_1$ to $C_{10}$ hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include benzyl, phenethyl, cyclohexylmethyl, cyclopropylmethyl, cyclobutylmethyl, allyl and camphoryl.

Acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, cyclobutane, cyclopentane, cyclohexane, benzene, cyclohexene and cyclohexadiene; ($C_8$-$C_{12}$) carbopolycycle refers to such systems as norbornane, decalin, indane, adamantane and naphthalene. Carbocycle, if not otherwise limited, refers to monocycles, bicycles and polycycles.

Heterocycle means a cycloalkyl or aryl residue in which one to three of the carbons is replaced by a heteroatom such as oxygen, nitrogen or sulfur. Heteroaryls form a subset of heterocycles. Examples of heterocycles include pyrrolidine, pyrazole, pyrrole, imidazole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, pyrazine, thiophene, furan, oxazole, oxazoline, isoxazole, dioxane, tetrahydrofuran and the like.

As used herein, the term "optionally substituted" may be used interchangeably with "unsubstituted or substituted". The term "substituted" refers to the replacement of one or more hydrogen atoms in a specified group with a specified substituent. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(═O)O-alkyl], alkoxycarbonylamino [HNC(═O)O-alkyl], carboxamido [—C(═O)NH$_2$], alkylaminocarbonyl [—C(═O)NH-alkyl], cyano, acetoxy, nitro, amino, alkylamino, dialkylamino, mercapto, alkylthio, alkylsulfinyl, alkylsulfonyl, benzyl, phenoxy, and benzyloxy. Although in most cases of "optionally substituted" residues, 1, 2 or 3 hydrogen atoms are replaced with a specified substituent, in the case of fluoroalkyl residues, more than three hydrogen atoms can be replaced by fluorine; indeed, all available hydrogen atoms could be replaced by fluorine, e.g. perfluoropropyl. In most cases, $C_1$ to $C_6$ alkyl residues or $C_1$ to $C_4$ alkyl residues are preferred as substituents.

The compounds described herein may contain one or more asymmetric centers in ring A and/or in the $R^x$ groups, and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

Likewise, all tautomeric forms and resonance structures are also intended to be included. For example, the structural representation of subgenus IIa can be presented either as the exocyclic iminium ion or the endocyclic iminium ion:

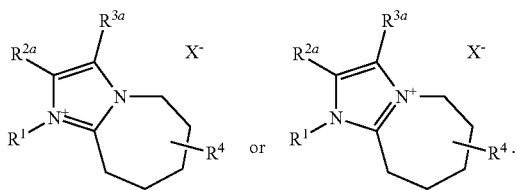

The two are equivalent.

As used herein, and as would be understood by the person of skill in the art, the recitation of "a compound"—unless expressly further limited—is intended to include salts of that compound. In a particular embodiment, the term "compound of formula I" refers to the pharmaceutically acceptable salt.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include, for example, $^2H$, $^3H$, $^{11}C$, $^{13}C$, $^{14}C$, $^{15}N$, $^{35}S$, $^{18}F$, $^{36}Cl$, $^{123}I$, $^{125}I$, $^{131}I$, and $^{133}I$. Compounds that contain those radioisotopes and/or other radioisotopes of other atoms are within the scope of this invention. Compounds containing $^3H$, $^{14}C$ and iodine radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formulae I and II of this invention can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

When the compounds of formula I, II or III are to be employed as antitumor agents in vivo, they may be administered as the raw chemical, but it is preferable to present them as a pharmaceutical composition. According to a further aspect, the present invention provides a pharmaceutical composition comprising a compound of formula II or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical or parenteral administration. For example, they may be given intravenously, intraarterially, subcutaneously, and directly into the CNS—either intrathecally or intracerebroventricularly.

Formulations include those suitable for oral, parenteral (including subcutaneous, intradermal, intramuscular, intravenous and intraarticular), rectal and topical (including dermal, buccal, sublingual and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS)

or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

As used herein, the terms "treatment" or "treating," or "palliating" or "ameliorating" refer to an approach for obtaining beneficial or desired results including but not limited to therapeutic benefit. By therapeutic benefit is meant eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder. The compositions may be administered to a patient at risk of developing a particular disease, or to a patient reporting one or more of the physiological systems of a disease, even though a diagnosis of this disease may not have been made.

The compounds employed in the methods described herein may be purchased from the following vendors: Life Chemicals, MolPort, Princeton Biomolecular Research Inc., and Sigma-Aldrich. Alternatively, they may be synthesized by methods well-known in the art. For example, a series of papers from the laboratory of A. M. Demchenko describes the syntheses of many imidazobicycles having a quaternary nitrogen [e.g. (1) Russian Journal of General Chemistry (Translation of Zhurnal Obshchei Khimii) (2001), 71, 1759-1763; (2) Chemistry of Heterocyclic Compounds (Translation of Khimiya Geterotsiklicheskikh Soedinenii) (2003), 39, 1084-1089; (3) Chemistry of Heterocyclic Compounds (2001), 37, 1054-1056; (4) Dopovidi Natsional'noi Akademii Nauk Ukraini (2000), 144-147; (5) Pharmaceutical Chemistry Journal (Translation of Khimiko-Farmatsevticheskii Zhurnal) (1999), 33, 421-423; (6) Russian Journal of General Chemistry (1997), 67, 1775-1781; (7) Chemistry of Heterocyclic Compounds (1997), 33, 724-727; (8) Ukrainskii Khimicheskii Zhurnal (Russian Edition) (1996), 62, 42-47; and (9) Zhurnal Prikladnoi Khimii (Sankt-Peterburg) (1996), 69, 1501-1504]. The contents of these articles is incorporated herein by reference. In accordance with the teachings of Demchenko, 2-arylazacycle amidines are condensed with phenacyl halides to produce compounds of the genus I:

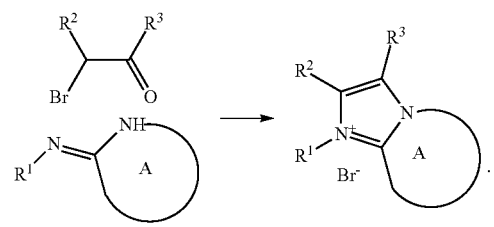

For example:

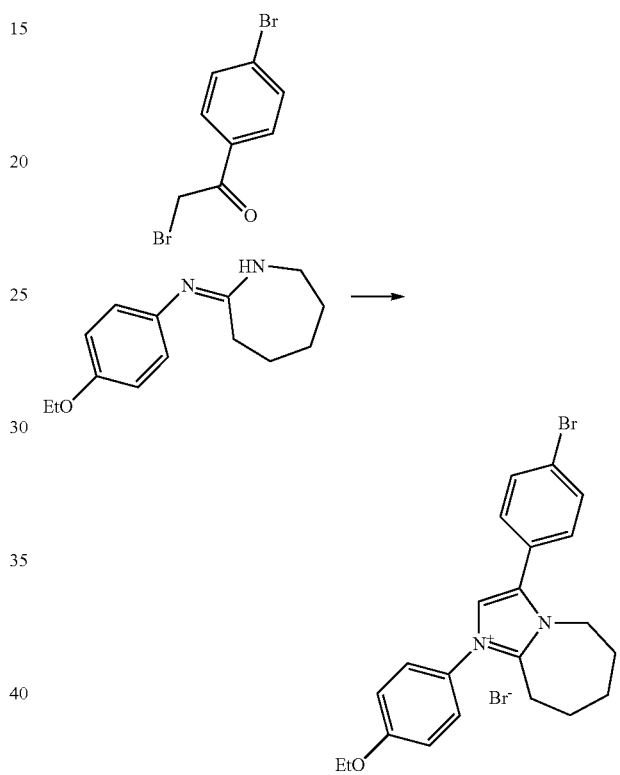

In like manner the other compounds in the Table 1 below may be synthesized.

Preparation of compounds A-19 and A-18

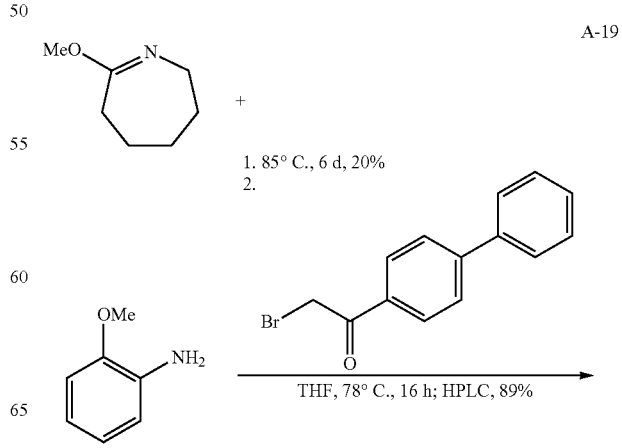

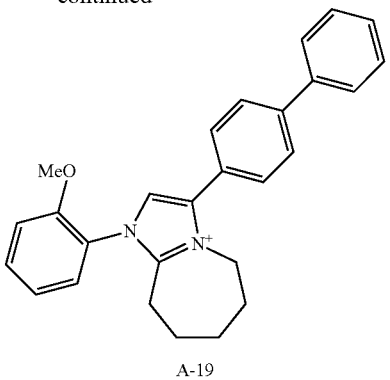

A-19

A mixture of o-anisidine (1.57 mL, 13.9 mmol, 1.00 equiv) and 7-methoxy-3,4,5,6-tetrahydro-2H-azepine (2.00 mL, 13.9 mmol, 1 equiv) was heated to 85° C. and stirred under a nitrogen atmosphere for 6 days. The resulting tan precipitate was collected by vacuum filtration and washed with 3×3 mL $Et_2O$ to yield N-(2-methoxyphenyl)-3,4,5,6-tetrahydro-2H-azepin-7-amine as a pale tan solid (608 mg, 20%).

1-([1,1'-biphenyl]-4-yl)-2-bromoethan-1-one (126 mg, 0.458 mmol, 1.00 equiv) was added to a pressure vessel charged with a suspension of N-(2-methoxyphenyl)-3,4,5,6-tetrahydro-2H-azepin-7-amine (100 mg, 0.458 mmol, 1 equiv) in THF (0.916 mL) and the vessel was sealed and placed on an oil bath at 78° C. The reaction mixture became a clear yellow solution within 15 min. The vessel was maintained at 78° C. for 16 h, then allowed to cool to room temperature, and the solution was concentrated under reduced pressure to yield a pale brown oily residue.

The residue was dissolved in acetic anhydride (1.35 mL) in a pressure vessel, and the vessel was sealed and maintained on an oil bath at 120° C. for 5 h. The vessel was then allowed to cool to room temperature, the deep brown solution was concentrated under reduced pressure, and the residue was purified by flash column chromatography on silica gel (eluent: gradient, 2.5→5% MeOH in $CH_2Cl_2$, diam. 1.5 cm, ht. 6 cm) to yield A-18 (X=Br) as a brown oil. Further purification by HPLC (Agilent Microsorb 300-5 C18 Dynamax 250×21.4 mm, gradient: 20→75% MeCN (0.1% TFA) in $H_2O$ (0.1% TFA), 35 min, 5→12.5 mL/min, tR=12.5 min) provided A-19 (X=$O_2CCF_3$, 207 mg, 89%) as a pale tan oil.

$^1$H NMR (400 MHz, $CDCl_3$, 25° C.) 7.75 (d, J=8.0 Hz, 2H, NCHCCH), 7.45-7.63 (m, 8H), 7.39 (tt, J=7.4, 1.2 Hz, 1H, $(CH)_2CH(CH)_2$), 7.11-7.16 (m, 2H, MeOCCH, MeOCCHCH), 7.11 (s, 1H, NCHCN), 4.22-4.40 (m, 2H, $CNCH_2$), 3.88 (s, 3H, $OCH_3$), 2.90-3.04 (m, 2H, $CH_2CN$), 1.64-2.10 (m, 6H, $CH_2(CH_2)_3CH_2$).

$^{13}$C NMR (100 MHz, $CDCl_3$, 25° C.) 153.6, 150.9, 143.7, 139.8, 134.9, 133.2, 130.7, 130.7, 129.3, 129.3, 128.4, 128.4, 128.3, 128.3, 127.4, 127.4, 123.8, 122.7, 122.0, 119.9, 112.7, 56.3, 48.1, 29.7, 27.1, 25.5, 23.7.

A-18 was prepared according to the procedure described for A-19 (X=$O_2CCF_3$: 214 mg, yield: 98% from N-(2-methoxyphenyl)-3,4,5,6-tetrahydro-2H-azepin-7-amine).

$^1$H NMR (400 MHz, $CDCl_3$, 25° C.) 7.55 (td, J=7.9, 1.5 Hz, 1H, MeOCCCH), 7.45 (dd, J=8.2, 1.5 Hz, 1H, MeOCCHCH), 7.34 (d, J=8.6 Hz, 2H, NCHCCCH), 7.13 (d, J=8.2 Hz, 1H, $CH_3OCCH$), 7.10-7.14 (m, 1H, NCHCH), 7.00 (d, J=8.6 Hz, 2H, $CH_3CH_2OCCH$), 7.01 (s, 1H, NCHCN), 4.24-4.29 (m, 2H, $NCH_2$), 4.06 (q, J=7.0 Hz, 2H, $OCH_2CH_3$), 3.86 (s, 3H, $OCH_3$), 2.87-3.02 (m, 2H, $CH_2CN$), 1.62-2.09 (m, 6H, $CH_2(CH_2)_3CH_2$), 1.41 (t, J=7.0 Hz, 3H, $OCH_2CH_3$).

$^{13}$C NMR (100 MHz, $CDCl_3$, 25° C.) 160.8, 153.3, 150.1, 134.9, 132.9, 131.5, 131.5, 128.1, 122.5, 121.6, 119.2, 116.3, 115.3, 115.3, 112.4, 63.8, 56.0, 47.6, 29.4, 26.8, 25.3, 23.5, 14.6.

Assays and Test Results

Sufu-KO-LIGHT cells were derived from Sufu knockout mouse embryonic fibroblasts according to the method of Chen et al. [Genes Dev. 2009; 23(16):1910-28.] The cells were co-transfected with the zeocin resistance vector (pVgRXR, Invitrogen) and a firefly luciferase reporter driven by eight Gli binding sites and a γ-crystallin basal promoter (8XGliBS-FL) [see Sasaki et al. Development. 1997; 124(7):1313-22.2]. Selection with 400 µg/mL zeocin (Invitrogen, R250-01) and cell cloning were then conducted to generate the Sufu-KO-LIGHT line, which demonstrates constitutive Hh pathway activation that is sensitive to HPI-1 treatment. Sufu-KO-LIGHT cells were cultured in DMEM (Invitrogen, 11965) containing 10% (v/v) fetal bovine serum (Invitrogen, No. 26140), 150 µg/mL zeocin (Invitrogen, R250-01), 1 mM sodium pyruvate (Invitrogen, 11360) and 1× PenStrep (Gibco, 15140).

Shh-LIGHT2 cells [see Taipale et al. Nature. 2000; 406 (6799):1005-9], an NIH-3T3-based cell line containing a stably integrated Gli-responsive firefly luciferase reporter (8XGliBS-FL) and constitutive Renilla luciferase reporter (pRLTK, Promega), were cultured in DMEM (Invitrogen, 11965) containing 10% (v/v) calf serum [the American Type Culture Collection (ATCC), 30-2030], 150 µg/mL zeocin (Invitrogen, R250-01), 400 µg/mL G418 (Invitrogen, 11811), 1 mM sodium pyruvate (Invitrogen, 11360) and 1× PenStrep.

C3H10T(1/2) cells were obtained from ATCC and cultured in DMEM (Invitrogen, 11965) containing 10% (v/v) fetal bovine serum (Invitrogen, No. 26140), and 1× PenStrep (Gibco, 15140).

NIH-3T3 cells were obtained from ATCC and cultured in DMEM (Invitrogen, 11965) containing 10% (v/v) calf serum (ATCC, 30-2030), 1 mM sodium pyruvate (Invitrogen, 11360) and 1× PenStrep (Gibco, 15140).

Shh-EGFP cells [see Hyman et al. Proc Natl Acad Sci USA. 2009; 106(33):14132-7], an NIH-3T3-based cell line containing a stably integrated Gli-dependent enhanced green fluorescent protein reporter (Shh-EGFP) and zeocin resistance vector (pVgRXR, Invitrogen), were cultured in DMEM (Invitrogen, 11965) containing 10% (v/v) calf serum (ATCC, 30-2030), 150 µg/mL zeocin (Invitrogen, R250-01), 1 mM sodium pyruvate (Invitrogen, 11360) and 1× PenStrep (Gibco, 15140).

Wnt-LIGHT cells [see Hyman et al. Proc Natl Acad Sci USA. 2009; 106(33):14132-7], a L-cell-based cell line containing a stably integrated TCF/LCF-dependent firefly luciferase reporter (SuperTopFlash), constitutive Renilla luciferase reporter (pRLSV40, Promega), and geneticin resistance vector (pcDNA3, Invitrogen), were cultured in DMEM (Invitrogen, 11965) containing 10% (v/v) fetal bovine serum (Invitrogen, No. 26140), 400 µg/mL G418 (Invitrogen, 11811) and 1× PenStrep (Gibco, 15140).

Gli1 null cells [see Lipinski et al. BMC Cell Biol. 2008; 9:49], an immortalized mouse embryonic fibroblast cell line lacking the Gli1 gene, were cultured in DMEM (Invitrogen, 11965) containing 10% (v/v) calf serum (ATCC, 30-2030), 1 mM sodium pyruvate (Invitrogen, 11360), 1× PenStrep (Gibco, 15140) and 1×MEM non-essential amino acids solution (11140, Invitrogen).

All test compounds were dissolved in DMSO at 50 mM, serially diluted by 1:3, 1:4 or 1:5 in a 96-well translucent microplate (Greiner bio-one, 650201) and stored at −20° C. These serial dilutions were added to assay media freshly with final DMSO concentration of 0.2% (v/v).

The Sufu-KO-LIGHT cell assay provides a measure of Hh pathway activity and cytotoxicity. Sufu-KO-LIGHT cells were seeded into a 96-well plate (35,000 cells/well), cultured to confluency for 24 hrs and then incubated with test compounds in DMEM without phenol red (Invitrogen, 26140) containing 0.5% (v/v) fetal bovine serum (Invitrogen, No. 26140), 150 μg/mL zeocin (Invitrogen, R250-01), 1 mM sodium pyruvate (Invitrogen, 11360), 1× PenStrep (Gibco, 15140) for 16 hrs. Bright Glo (Promega, E2620) reagent (50 μL/well) was added to the cells, and luciferase activities were determined on a microplate luminometer (Veritas). To assess cytotoxicity, after 15 hrs of incubation with test compounds, CellTiter 96 AQueous One Solution Cell Proliferation Assay (Promega, G3580) reagent (20 μL/well) was added. Cell viability was determined by measuring absorption at 490 nm after 1 hr of incubation on a microplate spectrophotometer (Benchmark Plus, Bio-Rad). Biological triplicates were analyzed for each test compounds.

The Shh-LIGHT2 cell assay provides a measure of Hh pathway activity. ShhN-conditioned medium was prepared by culturing a Shh-N-producing HEK 293 cell line [see Chen et al. Proc Natl Acad Sci USA. 2002; 99(22):14071-6] in DMEM (Invitrogen, 11965) containing 10% (v/v) calf serum (ATCC, 30-2030), 1 mM sodium pyruvate (Invitrogen, 11360) and 1× PenStrep (Gibco, 15140). After the cells reached 90% confluency, the medium was exchanged to DMEM (Invitrogen, 11965) containing 2% (v/v) calf serum (ATCC, 30-2030), 1 mM sodium pyruvate (Invitrogen, 11360) and 1× PenStrep (Gibco, 15140), and the resulting ShhN-conditioned medium was collected 24 hrs later and filtered through a 0.22-μm membrane. Shh-LIGHT2 cells were seeded into a 96-well plate (35,000 cells/well), cultured to confluency for 32 hrs and then incubated with test compounds in DMEM (Invitrogen, 11965) containing 0.5% (v/v) calf serum (ATCC, 30-2030), 150 μg/mL zeocin (Invitrogen, R250-01), 400 μg/mL G418 (Invitrogen, 11811), 1 mM sodium pyruvate (Invitrogen, 11360), 1× PenStrep (Gibco, 15140) and 10% (v/v) ShhN-conditioned medium for 30 hrs. The cells were lysed with passive lysis buffer (50 μL/well), and 10 μL of the obtained lysate were analyzed for firefly and *Renilla luciferase* activities using Dual-Luciferase Reporter Assay System (Promega, E1960) (50 μL/well of each reagent) on a microplate luminometer (Veritas). Biological triplicates were analyzed for each test compounds.

The Wnt-LIGHT cell assay provides a measure of Wnt pathway activity. Wnt3a-conditioned medium was prepared by culturing Wnt3a-expressing L cells obtained from ATCC in DMEM (Invitrogen, 11965) containing 10% (v/v) fetal bovine serum (Invitrogen, No. 26140) and 1× PenStrep (Gibco, 15140). After the cells reached 70% confluency, the medium was exchanged to fresh medium, and the resulting Wnt3a-conditioned medium was collected 24 hrs later and filtered through a 0.22-μm membrane. Wnt-LIGHT cells were seeded into a 96-well plate (12,000 cells/well), cultured for 24 hrs and then incubated with test compounds in DMEM (Invitrogen, 11965) containing 10% (v/v) fetal bovine serum (Invitrogen, No. 26140), 50% (v/v) Wnt3a-conditioned medium, 400 μg/mL G418 (Invitrogen, 11811), 1 mM sodium pyruvate (Invitrogen, 11360) and 1× PenStrep (Gibco, 15140) for 24 hrs. The cells were lysed with passive lysis buffer (50 μL/well), and 10 μL of the obtained lysate were analyzed for firefly and *Renilla luciferase* activities using Dual-Luciferase Reporter Assay System (Promega, E1960) (50 μL/well of each reagent) on a microplate luminometer (Veritas). Biological triplicates were analyzed for each test compounds.

The C3H10T(1/2) cell assay provides a measure of Hh pathway-dependent osteoblast differentiation. C3H10T(1/2) cells were seeded into a 96-well plate (20,000 cells/well), cultured for 30 hrs and then incubated with test compounds in DMEM (Invitrogen, 11965) containing 0.5% (v/v) fetal bovine serum (Invitrogen, 26140), 1× PenStrep (Gibco, 15140), and 10% (v/v) Shh-N-conditioned medium for 44 hrs. The cells were lysed with lysis buffer (50 μL/well) containing 50 mM Tris-HCl, pH 9.5, 150 mM NaCl, 50 mM MgCl2, and 1% (v/v) Triton X-100. 10 μL of the obtained lysate were analyzed for alkaline phosphatase activities using CDP-Star Substrate (Applied Biosystems, T2146) reagent (50 μL/well) on a microplate luminometer (Veritas). Biological triplicates were analyzed for each test compounds.

Overexpression of Gli2 in Gli1 null cells provides a measure of Gli2-induced pathway activity. pcDNA-derived Gli2 expression vectors (200 ng/well) and a 1:19 mixture (total 200 ng/well) of constitutive *Renilla luciferase* reporter (pRLTK, Promega) and firefly luciferase reporter (8XGliBS-FL) were mixed with FuGene HD transfection reagent (1.2 μL/well, Promega, E2311) in Opti-MEM Reduced-Serum Medium with GLutaMAX (Invitrogene, 51985) at a total volume of 25 μL/well. Gli1−/− mouse embryonic fibroblasts were dissociated in culture medium at 800,000 cells/mL, and 1.75 mL (1,400,000 cells) were incubated with the transfection reagent-DNA mix (1.4 mL) prepared above for 3 min. After addition of the culture medium (19.25 mL), the cells (0.4 mL/well, 25,000 cells/well) were plated into 24-well plates and cultured for 24 hrs. After the medium was exchanged to fresh medium, the cells were grown to confluence (24 hrs) and then incubated with test compounds in DMEM (Invitrogen, 11965) containing 0.5% (v/v) calf serum, 1× PenStrep (Gibco, 15140) and 1 mM sodium pyruvate (Invitrogen, 11360) for 24 hrs. The cells were lysed with passive lysis buffer (200 μL/well), and 10 μL of the obtained lysate were analyzed for firefly and *Renilla luciferase* activities using Dual-Luciferase Reporter Assay System (Promega, E1960) (50 μL/well of each reagent) on a microplate luminometer (Veritas). Biological triplicates were analyzed for each test compound.

Overexpression of Gli1 or Gli2 in NIH-3T3 cells provides a measure of Gli1- or Gli1/Gli2-induced pathway activity, respectively. NIH 3T3 cells were seeded into a 24-well plate (35,000 cells/well) and cultured for 30 hrs. The cells were co-transfected with pcDNA-derived Gli1 or Gli2 expression vectors (220 ng/well) and a 1:15 mixture (total 80 ng/well) of constitutive *Renilla luciferase* reporter (pRLTK, Promega) and firefly luciferase reporter (8XGliBS-FL), using TransIT-LT1 transfection reagent (1.5 μL/well, Minis Bio, MIR 2300) and Opti-MEM Reduced-Serum Medium (50 μL/well, Invitrogen, 31985) according to manufacturer's protocol and cultured for 24 h. After the medium was exchanged to fresh medium, the cells were grown to confluence (24 hrs) and incubated with test compounds in DMEM (Invitrogen, 11965) containing 0.5% (v/v) calf serum, 1× PenStrep (Gibco, 15140) and 1 mM sodium pyruvate (Invitrogen, 11360) for 24 hrs. The cells were lysed with passive lysis buffer (200 μL/well), and 10 μL of the obtained lysate were analyzed for firefly and *Renilla luciferase* activities using Dual-Luciferase Reporter Assay System (Promega, E1960) (50 μL/well of each reagent) on a microplate luminometer (Veritas). Biological triplicates were analyzed for each test compounds.

Quantification of Gli1 mRNA levels in NIH-3T3 cells provides a measure of endogenous Hh target gene expression. NIH 3T3 cells were seeded into 96-well plates (36,000 cells/well), cultured to confluency for 24 hrs and then incubated with test compounds in DMEM (Invitrogen, 11965) containing 0.5% (v/v) calf serum (ATCC, 30-2030), 1 mM sodium pyruvate (Invitrogen, 11360), 1× PenStrep (Gibco, 15140) and 10% (v/v) ShhN-conditioned medium for 24 hrs. The cells were lysed and the lysate was used to prepare cDNA using a Cells-to-CT kit (Ambion) according to the manufacturer's protocols. The cDNA was then quantified with Gli1 and GAPDH Taqman probes (Mm00494645m1 and Mm99999914g1, Applied Biosystems) on a Roche Lightcycler 480, using the 2nd derivative/maximum method to obtain Ct values. Biological triplicates were analyzed for each test compounds.

NIH 3T3 cells were also employed in a Smo trafficking assay. NIH 3T3 cells were seeded, treated with test compounds, fixed and blocked in the same way described below. The coverslips were incubated in blocking buffer containing rabbit anti-Smo [see Rohatgi et al. Science. 2007; 317 (5836):372-6] and mouse monoclonal anti-N-acetylated-α-tubulin (clone 6-11B-1, 1:5000 dilution; Sigma-Aldrich, T7451) for 1 hr at room temperature. The cells were then washed three times with PBS and incubated in blocking buffer containing Alexa Fluor 488-conjugated donkey polyclonal anti-rabbit IgG antibody (1:2000 dilution; Invitrogen, A-21206), Alexa Fluor 594-conjugated donkey polyclonal anti-mouse IgG antibody (1:2000 dilution; Invitrogen, A-21203) for 1 hr. After washed three times with PBS, the coverlsips were mounted onto slides using Prolong Gold Antifade Reagent with DAPI (Invitrogen, P36931). The cells were imaged using a Plan Apochromat 63×/1.4-0.6 oil immersion objective on an upright Leica DM4500B compound microscope. Ciliary Smo levels were quantified by determining total pixel intensity within a circular region manually placed at the distal end of each cilium and subtracting background fluorescence in an adjacent region of equivalent size. Ciliary Smo levels were quantified by designating ciliary regions according to N-acetylated-α-tubulin staining manually. The ciliary regions were then transferred to the corresponding images of Smo antibody staining, and the average pixel intensity was quantified by determining total pixel intensity within the region and subtracting background fluorescence in an adjacent region of equivalent size. Total of 30 cilia from three coverslips were analyzed to determine the average ciliary Smo level for each experimental condition as a measure of Smo trafficking.

NIH 3T3 cells were also employed in an assay to quantify Gli2 trafficking NIH-3T3 cells were seeded into 24-well plates containing poly-D-lysine-coated 12-mm glass coverslips (65,000 cells/well) and cultured for 24 hrs. The cells were then cultured in DMEM (Invitrogen, 11965) containing 0.5% (v/v) calf serum (ATCC, 30-2030), 1 mM sodium pyruvate (Invitrogen, 11360) and 1× PenStrep (Gibco, 15140) for 20 hrs to promote primary cilia formation. The cells were next treated for 4 hrs with test compounds at concentrations 10-fold greater than their IC50s or 0.2% (v/v) DMSO (vehicle) in the same medium described above. Each compound or vehicle treatment was conducted in biological triplicates in the presence or absence of 10% (v/v) ShhN-conditioned medium. The cells were subsequently fixed in PBS containing 4% (v/v) paraformaldehyde for 12 min at room temperature, washed three times with PBS, permeabilized in PBS containing 0.5% (v/v) Triton X-100 for 5 min, and washed again twice in PBS. After blocking overnight at 4° C. in PBS containing 1% (w/v) bovine serum albumin (Sigma, A7030), the coverslips were incubated in blocking buffer containing goat polyclonal anti-Gli2 antibody (1:150 dilution; R & D Systems, AF3635), and mouse monoclonal anti-N-acetylated-α-tubulin (clone 6-11B-1, 1:5000 dilution; Sigma-Aldrich, T7451) for 1 hr at room temperature. The cells were then washed three times with PBS and incubated in blocking buffer containing DyLight 488-conjugated donkey polyclonal anti-goat IgG antibody (3 μg/mL; Jackson ImmunoResearch, 705-485-147), DyLight 594-conjugated donkey polyclonal anti-mouse IgG antibody (3 μg/mL; Jackson ImmunoResearch, 715-515-151) for 1 hr. After three PBS washes, the coverslips were mounted onto slides using Prolong Gold Antifade Reagent with DAPI (Invitrogen, P36931). The cells were imaged using a Plan Apochromat 63×/1.4-0.6 oil immersion objective on an upright Leica DM4500B compound microscope. Ciliary Gli2 levels were quantified by determining total pixel intensity within a circular region manually placed at the distal end of each cilium and subtracting background fluorescence in an adjacent region of equivalent size. A total of 30 cilia from three coverslips were analyzed to determine the average ciliary Gli2 level for each experimental condition as a measure of Gli2 trafficking.

A quantitative assessment of Hh ligand-dependent Gli3 processing was provided by the following assay: Shh-EGFP cells were seeded into 12-well plates at a density of 160,000 cells/well and cultured for 24 hrs in DMEM (Invitrogen, 11965) containing 10% (v/v) calf serum (ATCC, 30-2030), 150 μg/mL zeocin (Invitrogen, R250-01), 1 mM sodium pyruvate (Invitrogen, 11360) and 1× PenStrep (Gibco, 15140). The cells were next treated for 16 hrs with test compounds at concentrations 10-fold greater than their IC50s or 0.2% (v/v) DMSO (vehicle) in DMEM (Invitrogen, 11965) containing 0.5% (v/v) calf serum (ATCC, 30-2030) and antibiotics described above. Each compound or vehicle treatment was conducted in the presence or absence of 10% (v/v) Shh-N-conditioned medium. The cells were then lysed by incubation with SDS-PAGE loading buffer composed of 50 mM Tris-HCl, pH 6.8, 2% (w/v) SDS, 8% (v/v) glycerol, 100 mM DTT, 0.1 mg/mL bromophenol blue, EDTA-free protease inhibitor cocktail (Roche) and Phosstop (Roche) for 5 min in a cold room. The lysate were heated to 100° C. for 7 min, loaded onto 3-8% Criterion XT Tris-Acetate polyacrylamide gels (Bio-Rad, 345-0129), electrophoresed in XT Tricine buffer (Bio-Rad, 161-0790), and transferred onto PVDF membranes (EMD Millipore, IPVH304F0). The membranes were dehydrated with methanol and probed overnight at 4° C. with goat polyclonal anti-Gli3 antibody (1 μg/mL; R & D Systems, AF3690) in PBS containing 4% (w/v) non-fat dry milk and 0.01% (v/v) Tween-20 (immunoblot blocking buffer). The blots were then washed four times in PBS and incubated with horseradish peroxidase-conjugated bovine polyclonal anti-goat IgG antibody (0.16 μg/mL; Jackson ImmunoResearch, 805-035-180) in immunoblot blocking buffer for 1 hr at room temperature. The membranes were next washed four times in PBS and visualized using SuperSignal West Dura Extended Duration substrate (Thermo Scientific, 34076) and a ChemiDoc XRS imaging system (Bio-Rad). Band intensities of Gli3FL and Gli3R were quantified using ImageJ64 software (NIH), and three independent experiments were used to determine the average Gli3FL/Gli3R ratio for each compound.

| Cell line | Reporter | IC$_{50}$ (µM) |
|---|---|---|
| Sufu-KO-LIGHT | firefly luciferase | 1.42 ± 0.96 |
| Sufu-KO-LIGHT | cytotoxicity | No toxicity |
| Wnt-LIGHT w/ Wnt3a | firefly luciferase | No inhibition |
| Shh-LIGHT2 w/ ShhN | firefly luciferase | 6.6 |
| C3H10T(½) w/ ShhN | alkaline phosphatase | 5.2 ± 3.7 |
| NIH-3T3 w/ ShhN | Gli1 mRNA | 5 |
| Gli1-overexpressing NIH-3T3 | firefly luciferase | 0.16 |
| Gli2-overexpressing NIH-3T3 | firefly luciferase | 0.77 ± 0.88 |
| Gli2-overexpressing Gli1-/- | firefly luciferase | No inhibition |

The foregoing studies confirmed that A-1 inhibits Hh pathway activity in Sufu-KO-LIGHT cells, as well as NIH-3T3 cells stably transfected with the Gli-dependent firefly luciferase reporter (Shh-LIGHT2 cells) and stimulated with medium containing the Shh N-terminal domain (ShhN). The compound blocked the ability of ShhN-conditioned medium to differentiate C3H10T1/2 cells into alkaline-phosphatase-expressing osteoblasts and inhibited the ShhN-dependent expression of endogenous target genes (Gli1). Studies also confirmed that A-1 was not generally cytotoxic and that it did not inhibit Wnt signaling compound.

The ability of A-1 to inhibit Hh reporter in Sufu-KO-LIGHT cells indicates that it acts at the level of the Gli transcription factors within the pathway. Consistent with this downstream site of action, the compound did not affect Smo localization in Hh-responsive cells. ShhN stimulation causes Smo to accumulate within the primary cilium, and the known Smo inhibitor cyclopamine also alters Smo trafficking. A-1, however, did not affect Smo localization. Similarly, ShhN treatment causes Gli2 to accrue at the ciliary distal tip in a cyclopamine-sensitive manner, but A-1 did not inhibit this process. These results suggest that A-1 does not prevent Gli transcription factor activation. While ShhN stimulation caused the Gli3FL/Gli3R ratio to increase and cyclopamine abrogated that effect, A-1 did not perturb Gli3 processing. Nor did the compound prevent Gli3FL phosphorylation.

Compound A-1 potently blocked exogenous Gli1 activity but only partially inhibited Hh reporter expression induced by exogenous Gli2. Since Gli1 is a Hh target gene that will be expressed in response to Gli2 overexpression, it is reasonable to assume that this partial effect could reflect action of A-1 on Gli1 but not Gli2. Consistent with this model, A-1 was not able to inhibit Gli2-induced Hh reporter expression in cells lacking Gli1. Thus, the evidence indicates that A-1 is representative of a class of specific inhibitors of Gli1. Representative results of studies in vitro on other species within the genus I are outlined in Tables 1 to 3.

TABLE 1

| R$^1$ | R$^{2a}$ | R$^{3a}$ | Comp. | IC$_{50}$ (µM) |
|---|---|---|---|---|
| 4-EtO-phenyl | H | 4-Br-phenyl | A-1 | 1.42 ± 0.96 |
| phenyl | H | 4-Br-phenyl | A-2 | 7.9 |
| 2-OMe-phenyl | H | 4-Br-phenyl | A-3 | 0.34 |
| 2,3-dihydro-1,4-benzodioxin-6-yl | H | 4-Br-phenyl | A-4 | 5.0 |

TABLE 1-continued
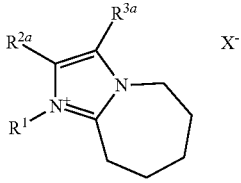
| R¹ | R²ᵃ | R³ᵃ | Comp. | IC$_{50}$ (μM) |
|---|---|---|---|---|
| 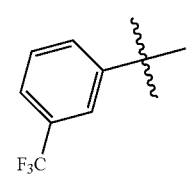 | H | 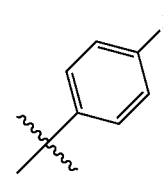 | A-5 | 12.3 |
| 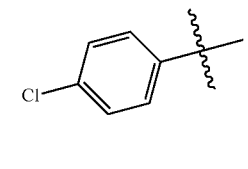 | H | 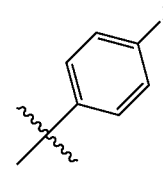 | A-6 | 11.7 |
| 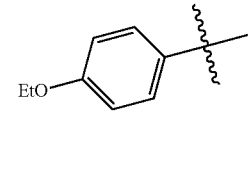 | H | 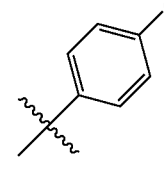 | A-7 | 3.0 |
| 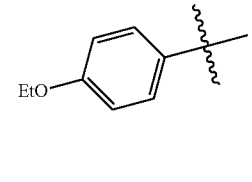 | H | 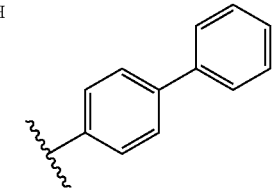 | A-8 | 0.19 ± 0.14 |
| 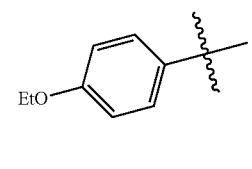 [SMILES: *c1ccc(OCC)cc1] | H | 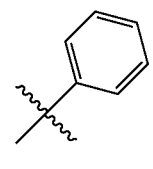 [SMILES: *c1ccccc1] | A-9 | 1.7 |
| 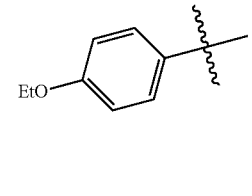 [SMILES: *c1ccc(OCC)cc1] | H | 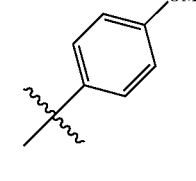 | A-10 | 2.5 |
| 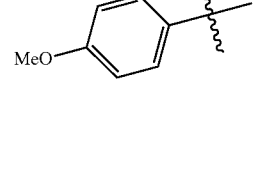 | H | 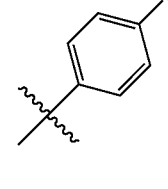 | A-11 | 2.5 |

TABLE 1-continued
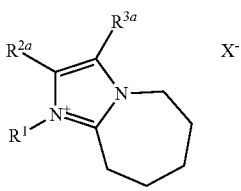
| R¹ | R²ᵃ | R³ᵃ | Comp. | IC$_{50}$ (μM) |
|---|---|---|---|---|
| 4-MeO-C₆H₄- | H | 4-OCF₂H-C₆H₄- | A-12 | 13.9 |
| 4-(HF₂CO)-C₆H₄- | H | 4-Cl-C₆H₄- | A-13 | 17.5 |
| 4-Br-C₆H₄- | H | 4-OMe-C₆H₄- | A-15 | 3.3 |
| 3-F₃C-C₆H₄- | H | 4-OEt-C₆H₄- | A-16 | 7.4 |
| 4-Et-C₆H₄- | H | 4-OCF₂H-C₆H₄- | A-17 | 2.9 |
| 2-OMe-C₆H₄- | H | 4-OEt-C₆H₄- | A-18 | 0.08 |
| 2-OMe-C₆H₄- | H | biphenyl-4-yl | A-19 | 0.03 |

TABLE 2

[Structure: imidazo-fused 7-membered ring with N+ bearing R1, C2 bearing R2a, C3 bearing R3a, with X- counterion]

| R¹ | R²ᵃ | R³ᵃ | Comp. | IC₅₀ (μM) |
|---|---|---|---|---|
| 4-EtO-C₆H₄- | 4-MeO-C₆H₄- | H | C-1 | 1.6 |
| 2-MeO-C₆H₄- | 4-MeO-C₆H₄- | H | C-2 | 3.1 |
| 4-Me-C₆H₄- | 4-MeO-C₆H₄- | H | C-3 | 4.2 |
| 4-Cl-C₆H₄- | 4-MeO-C₆H₄- | H | C-4 | 11.5 |
| 4-EtO-C₆H₄- | 4-EtO-C₆H₄- | Me | C-5 | 1.2 |
| 4-MeO-C₆H₄- | 4-Cl-C₆H₄- | H | C-6 | 11.7 |

TABLE 2-continued

| R¹ | R²ᵃ | R³ᵃ | Comp. | IC₅₀ (μM) |
|---|---|---|---|---|
| 4-MeO-C₆H₄- | 4-HF₂CO-C₆H₄- | H | C-7 | 6.3 |
| 4-MeO-C₆H₄- | C₆H₅- | H | C-8 | 4.1 |
| 4-Cl-C₆H₄- | 4-Cl-C₆H₄- | H | C-9 | 27.0 |

TABLE 3

| Structure | Comp. | IC₅₀ (μM) |
|---|---|---|
| 1-(4-EtO-C₆H₄)-3-phenyl-6,7-dihydro-5H-pyrrolo[2,1-b]imidazol-1-ium | D-1 | 0.96 |
| 1-(4-MeO-C₆H₄)-3-(4-MeO-C₆H₄)-2,3-dihydroimidazo[2,1-b]thiazol-4-ium | D-2 | 3.1 |
| 1-(4-MeO-C₆H₄)-3-(4-Me-C₆H₄)-2-methyl-2,3-dihydroimidazo[2,1-b]thiazol-4-ium | D-3 | 1.1 |

TABLE 3-continued

| Structure | Comp. | IC$_{50}$ (μM) |
|---|---|---|
| MeO–C₆H₄–[imidazo-thiazoline]–C₆H₄–Br (methyl-substituted) | D-4 | 2.6 |
| MeO–C₆H₄–[imidazo-thiazine]–C₆H₄–Cl | D-5 | 2.4 |
| MeO–C₆H₄–[imidazo-morpholine]–C₆H₄–OMe | D-6 | 14.1 |
| 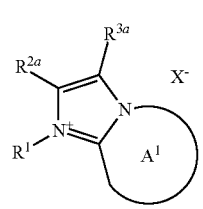 (OEt–C₆H₄–[pyrrolo-quinolinium]–C₆H₄–OMe, Br⁻) | E-1 | 0.14 |

The foregoing results in vitro predict utility against Hh pathway-dependent tumors. Representative compounds A-8 and E-1 have been tested in vivo.

Murine basal cell carcinomas (BCCs) were derived from Ptch1+/−; p53−/− mice subjected to UV radiation [Aszterbaum et al., Nat. Med. (1999) 5:1285-91]. A line resistant to the Smo antagonist SANT-1 was obtained by culturing the cells in media containing increasing concentrations of the inhibitor until the majority of cells were killed and resistant clones emerged.

Murine BCC allograft model: Ptch1+/−; K14:Cre-ER2; p53fl/fl mice were injected with tamoxifen (to knock out p53) at six weeks of age, and at 8 weeks of age they were given one dose of 4 Gy of ionizing radiation. After BCCs formed and grew to 5-7 mm in diameter (typically between 6-8 months of age), they were harvested and dissociated to prepare a cell suspension. A mixture of the cell suspension and Matrigel was then injected subcutaneously into NOD/SCID mice purchased from Jackson Laboratories. Once the allografted tumors became visible, they were monitored with digital calipers and the volume was estimated by the formula $(d^2) \cdot D/2$, where d is the smallest diameter of the tumor and D is the largest diameter. The compound was applied topically to the tumor as a DMSO solution (100 μL per application).

Murine medulloblastoma allograft model: Ptch1+/−; p53+/−; Math1:GFP mice were mated to generate pups with the appropriate genotype of Ptch1+/−; p53−/−; Math1:GFP. These mice will get medulloblastoma tumors when they are 6 to 10 weeks of age. The primary medulloblastoma tumors were harvested, dissected, dissociated by papain treatment and tissue trituration, and injected into the flanks of nude mice as a Matrigel mixture (50 μL of 2×107 tumor cells mixed with 50 μL of Matrigel). Secondary and tertiary tumors can subsequently be derived from these allografts as necessary. The length, width, and depth of each allograft were monitored, and compound testing began when the tumors reached a volume of 150 mm3 (approximately one week after tumors were first visible). The compounds were dissolved in a minimum volume of DMSO, and the DMSO solution was mixed with sterile corn oil so that the DMSO constituted less than 10% of the total volume. The drug was administered by intraperitoneal injection (50 μL), with each daily dose divided into two portions and administered at 12-hour intervals. The Smoothened antagonist vismodegib was administered at 50 mg/kg/day as a positive control.

Compound A-8 reduced BCC proliferation in dose-dependent fashion to 20% of control at 750 nM. A 0.01% solution reduced tumor volume by half in the murine BCC allograft model compared to control at day 14. Compound A-8 was able to block the proliferation of both the original BCC cell line and the SANT-1-resistant line. This indicates that these compounds could be used against tumors that have acquired resistance to Smo inhibitors. Compound E-1 at 2 mg/kg/day in the murine medulloblastoma allograft model reduced tumor volume by half compared to control at day 5.

The invention claimed is:

1. A pharmaceutical composition comprising a pharmaceutically acceptable carrier and a compound of formula II:

II wherein:
R$^1$ is chosen from optionally substituted aryl and optionally substituted heteroaryl;
R$^{2a}$ is chosen from H and (C$_1$-C$_4$)alkyl;
R$^{3a}$ is chosen from optionally substituted aryl and optionally substituted heteroaryl;
A$^1$ is (a) a fused, saturated ring of 7 members that contains no heteroatoms other than the nitrogen at the point of fusion, said saturated ring optionally substituted with one or two (C$_1$-C$_4$)alkyl residues or
(b) a fused bicycle, one ring of said fused bicycle being a saturated ring of 7 members that contains no heteroatoms other than the nitrogen at the point of fusion and a second ring of said fused bicycle being a benzene ring, said bicycle optionally substituted with one or two (C$_1$-C$_4$)alkyl residues; and
X is any counterion.

2. The pharmaceutical composition according to claim 1 wherein II has the formula IIa:

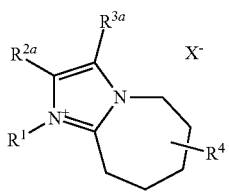

wherein $R^4$ is one or two $(C_1-C_4)$alkyl residues.

3. The pharmaceutical composition according to claim 1 wherein $R^1$ is phenyl or optionally substituted phenyl and $R^{3a}$ is phenyl or optionally substituted phenyl.

4. The pharmaceutical composition according to claim 3 wherein $R^1$ is phenyl or phenyl substituted with a substituent chosen from halogen, $(C_1-C_4)$alkyl, halo$(C_1-C_4)$alkyl, $(C_1-C_4)$alkoxy, halo$(C_1-C_4)$alkoxy, $(C_1-C_2)$alkylenedioxy and phenyl.

5. The pharmaceutical composition according to claim 4 wherein $R^{2a}$ is H or methyl and $R^{3a}$ is phenyl or phenyl substituted with a substituent chosen from halogen, $(C_1-C_4)$alkyl, halo$(C_1-C_4)$alkyl, $(C_1-C_4)$alkoxy, halo$(C_1-C_4)$alkoxy, $(C_1-C_2)$alkylenedioxy, and phenyl.

6. A compound of formula

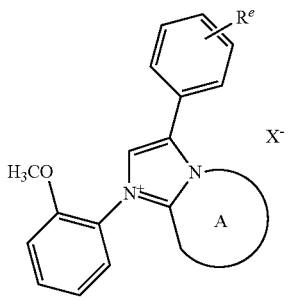

wherein
A is (a) a fused, saturated ring of 7 members that contains no heteroatoms other than the nitrogen at the point of fusion, said saturated ring optionally substituted with one or two $(C_1-C_4)$alkyl residues or (b) a fused bicycle, one ring of said fused bicycle being a saturated ring of 7 members that contains no heteroatoms other than the nitrogen at the point of fusion and a second ring of said fused bicycle being a benzene ring, said bicycle optionally substituted with one or two $(C_1-C_4)$alkyl residues; and $R^6$ is one or two substituents chosen independently from the group consisting of halogen, halo$(C_1-C_6)$alkyl, $(C_1-C_6)$alkyl, $(C_1-C_6)$acyl, $(C_1-C_6)$alkoxy$(C_1-C_6)$alkyl, hydroxy$(C_1-C_6)$alkyl, phenyl, benzenesulfonyl, hydroxy, $(C_1-C_6)$alkoxy, halo$(C_1-C_6)$alkoxy, oxaalkyl, carboxy, $(C_1-C_6)$alkoxycarbonyl, $(C_1-C_6)$alkoxycarbonylamino, carboxamido, cyano, acetoxy, nitro, amino, $(C_1-C_6)$alkylamino, $(C_1-C_6)$dialkylamino, mercapto, $(C_1-C_6)$alkylthio, $(C_1-C_6)$alkylsulfoxide, $(C_1-C_6)$alkylsulfonyl, benzyl, heterocyclyl, phenoxy, heteroaryloxy and benzyloxy, and X is any counterion;
with the proviso that when A is a fused, saturated ring of 7 members and $R^6$ is bromine or methoxy, $R^6$ is not in the para position.

7. The compound according to claim 6 of formula:

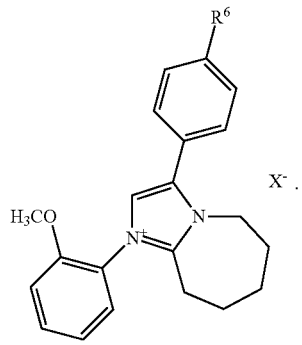

8. The compound according to claim 7 wherein $R^6$ is chosen from ethoxy and phenyl.

* * * * *